US00PP31787P2

(12) United States Plant Patent
Bryson et al.

(10) Patent No.: US PP31,787 P2
(45) Date of Patent: May 19, 2020

(54) ***POLEMONIUM* PLANT NAMED 'DUNKAL'**

(50) Latin Name: *Polemonium yezoense*
Varietal Denomination: DUNKAL

(71) Applicants: Graeme Bryson, Byt Falkirk (GB); Gillian Bryson, Byt Falkirk (GB)

(72) Inventors: Graeme Bryson, Byt Falkirk (GB); Gillian Bryson, Byt Falkirk (GB)

( * ) Notice: Subject to any disclaimer, the term of this patent is extended or adjusted under 35 U.S.C. 154(b) by 0 days.

(21) Appl. No.: 16/501,585

(22) Filed: May 3, 2019

(30) Foreign Application Priority Data

Jan. 22, 2019 (QZ) ..... PBR 20190214

(51) Int. Cl.
*A01H 5/02* (2018.01)
*A01H 6/70* (2018.01)

(52) U.S. Cl.
USPC ..... Plt./470
CPC ..... *A01H 6/70* (2018.05)

(58) Field of Classification Search
USPC ..... Plt./470
CPC ..... A01H 6/70; A01H 5/02
See application file for complete search history.

*Primary Examiner* — Keith O. Robinson
(74) *Attorney, Agent, or Firm* — Penny J. Aguirre

(57) ABSTRACT

A new cultivar of *Polemonium* plant named 'DUNKAL' that is characterized by its foliage that is variegated with light green, creamy white, dark green, and bright purple-pink when grown in full sun with foliage variegated with light pink rather than bright purple-pink when grown in shade, its multicolored foliage that is present on the basal leaves as well as on the cauline leaves and its abundance of large purple flowers that are bright purple when grown in full sun and slighter lighter purple in color when grown in shade.

3 Drawing Sheets

Botanical classification: *Polemonium yezoense.*
Variety denomination: 'DUNKAL'.

BACKGROUND OF THE INVENTION

The present invention relates to a new and distinct cultivar of *Polemonium yezoense* plant and will be referred to hereinafter by its cultivar name, 'DUNKAL'. The new cultivar of *Polemonium* is a hardy herbaceous perennial grown for landscape use.

'DUNKAL' was discovered by the Inventors in summer of 2010 as a chance seedling in a seedflat planted with seeds of *Polemonium yezoense* 'Purple Rain' (not patented) in Byt Falkirk, Scotland, The United Kingdom. The male parent is therefore unknown.

Asexual reproduction of the new cultivar was first accomplished by tissue culture using meristematic tissue under the direction of the Inventor in June of 2010 in Heerhugowaard, The Netherlands. Propagation by stem cuttings and tissue culture has determined the characteristics to be stable and reproduced true to type in successive generations.

SUMMARY OF THE INVENTION

The following traits have been repeatedly observed and are determined to be the characteristics of the new cultivar. These attributes in combination distinguish 'DUNKAL' as a unique cultivar of *Polemonium.*

1. 'DUNKAL' exhibits foliage that is variegated with light green, creamy white, dark green, and bright purple-pink when grown in full sun with foliage variegated with light pink rather than bright purple-pink when grown in shade.
2. 'DUNKAL' exhibits the multicolored foliage on the basal leaves as well as on the cauline leaves.

3. 'DUNKAL' exhibits an abundance of large purple flowers that are bright purple when grown in full sun and slighter lighter purple in color when grown in shade.

The female parent plant, 'Purple Rain', differs from 'DUNKAL' in having foliage that is green and tinged with reddish purple and bronze. 'DUNKAL' can also be compared to the *Polemonium* cultivars 'Stairway to Heaven' (U.S. Plant Pat. No. 15,187) and 'Brise d'Anjou' (U.S. Plant Pat. No. 9,781). Both are similar to 'DUNKAL' in having variegated foliage. 'Stairway to Heaven' differs from 'DUNKAL' in having foliage that is green and white and yellow margins and only a faint tinge of pink when grown in full sun, in having less flower spikes and less flowers per flower spike, and in having lighter colored flowers. 'Brise d'Anjou' differs from 'DUNKAL' in having foliage that is green with cream colored margins (lacks additional colors) and in having less flower spikes and less flowers per flower spike.

BRIEF DESCRIPTION OF THE DRAWINGS

The accompanying colored photographs illustrate the overall appearance and distinct characteristics of the new *Polemonium.*

The photograph in FIG. 1 were taken of plants 2 years in age as grown in a 25-cm container in full sun near Hertford, The United Kingdom. and provides a side view of 'DUNKAL' in early bloom before sunlight intensifies.

Figure 1:
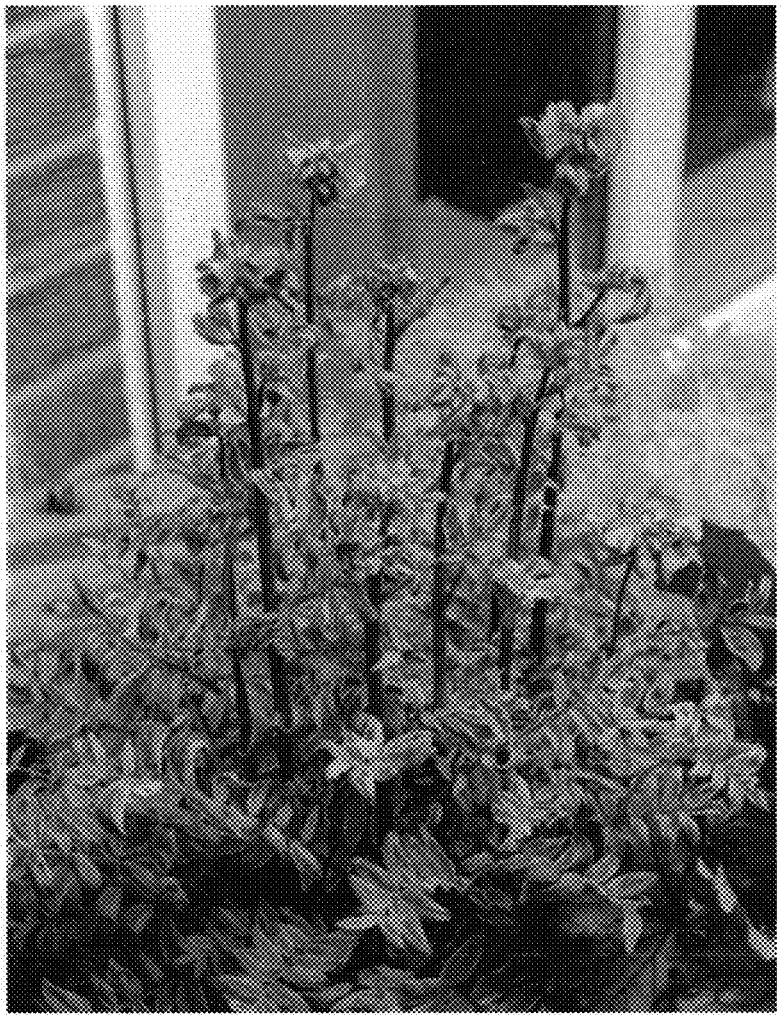
Figure 2:
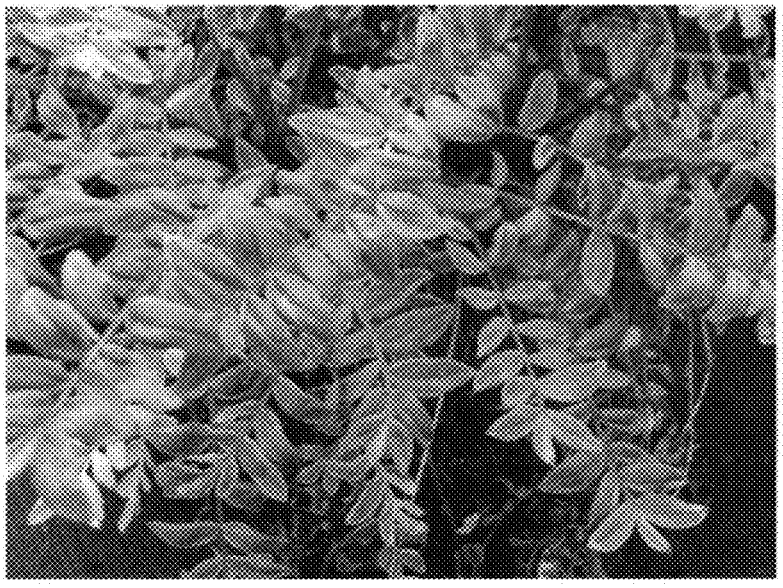

The photograph in FIG. 2 was taken of a plant 2 years in age as grown in a 2-liter container in Maldon, near Chelmsford, The United Kingdom and provides a close up view of the foliage emerging after overwintering.

Figure 3:
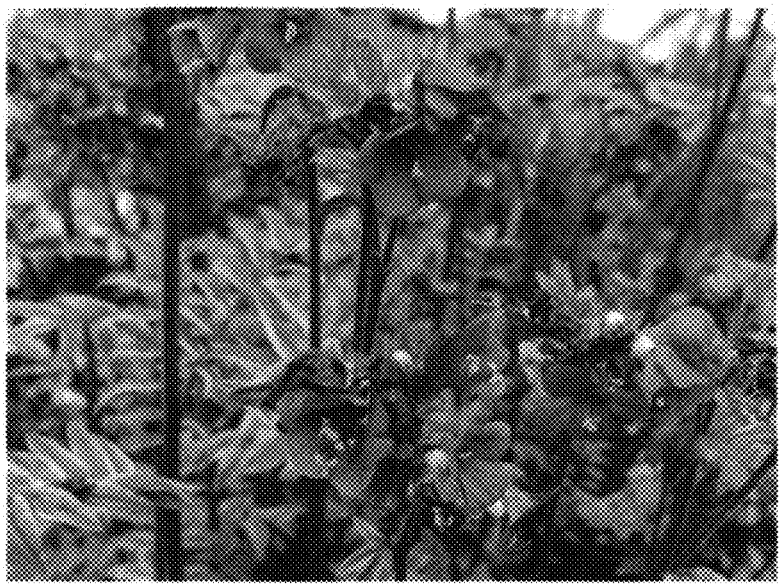

The photograph in FIG. 3 was taken of a plant 2 years in age as grown in a 5-liter container in Maldon, near Chelmsford, The United Kingdom and provides a close up view of the flowers grown in full sun.

Figure 4:
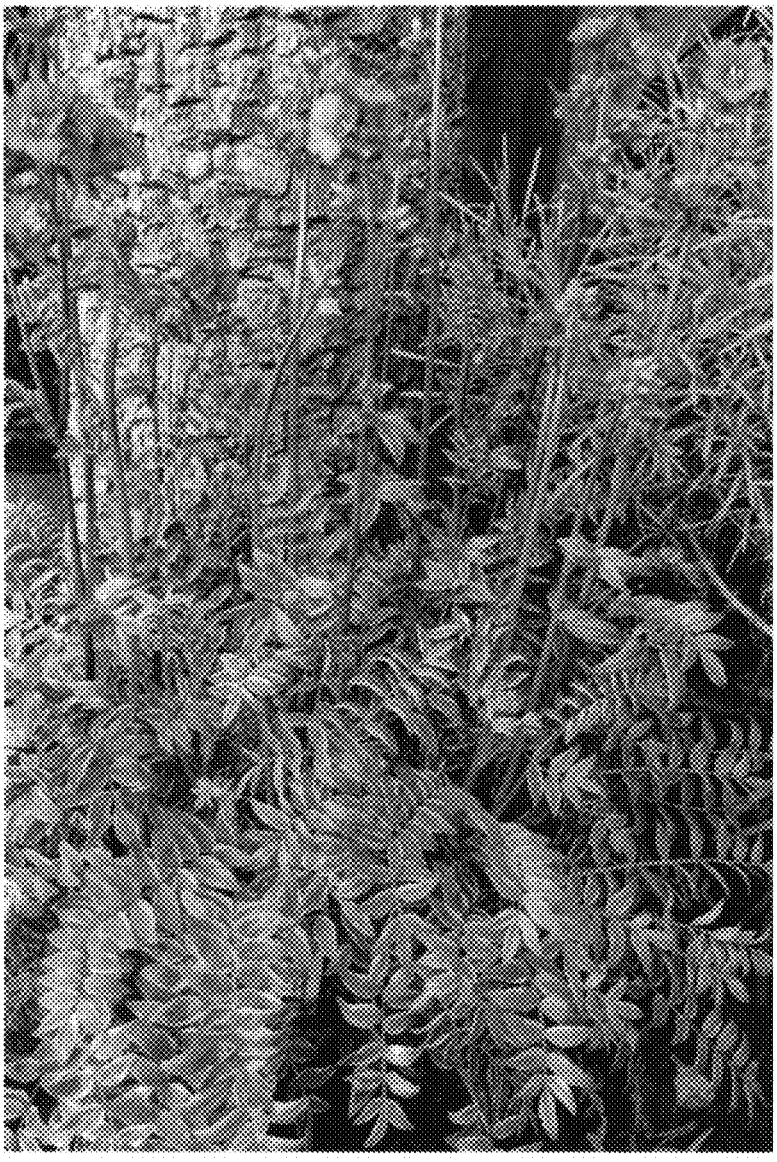

The photograph in FIG. 4 was taken of a plant 2 years in age as grown outdoors in a 5-liter container in Colchester, The United Kingdom and provides a view of a plant grown in mostly shade.

The colors in the photograph are as close as possible with the photographic and printing technology utilized. The color values cited in the detailed botanical description accurately describe the colors of the new *Polemonium.*

DETAILED BOTANICAL DESCRIPTION

The following is a detailed description of 1-year-old plants of the new cultivar as grown outdoors in 25-cm containers near Hertford, The United Kingdom, The United Kingdom. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General description:

*Blooming period.*—May to early July in The United Kingdom.

*Plant habit.*—Herbaceous perennial, mounded basal leaves with upright flowering stems emerging from basal leaves.

*Height and spread.*—Matures to an average 50 cm in height and 30 cm in width.

*Cold hardiness.*—At least to U.S.D.A. Zone 2.

*Diseases and pests.*—No susceptibility or resistance to pests has been observed, tolerance to some resistance has been observed to powdery mildew caused by species in the Erisiphaceae family.

*Root description.*—Fleshy.

*Propagation.*—Tissue culture.

*Root development.*—Unrooted cutting will root in 3 to 4 weeks and a young plant in a liner can be produced in about 8 weeks.

*Growth rate.*—Moderate.

Flowering stems:

*Stem shape.*—Sharply angled.

*Stem color.*—146D and can be suffused with 187A.

*Stem size.*—40 to 50 cm in length and 4 to 6 mm in diameter at mid stem.

*Stem surface.*—Glabrous.

*Internode length.*—Average of 4 cm.

Foliage description:

*Leaf division.*—Compound, odd-pinnate.

*Leaf arrangement.*—Basal with cauline leaves alternate.

*Leaf shape.*—Oblanceolate in outline (both basal and cauline leaves).

*Leaf size.*—Basal leaves range from 18 to 20 cm in length and 3 to 4 cm in width, cauline leaves range from 7 to 10 cm in length and 2.5 to 3.5 cm in width.

*Leaflet number.*—Up to 19 on basal leaves and 13 to 15 on cauline leaves.

*Leaflet arrangement.*—Variable (opposite or alternate).

*Leaflet shape.*—Narrow elliptic to lanceolate.

*Leaflet base.*—Cuneate.

*Leaflet apex.*—Acute with small cuspidate tip.

*Leaflet margin.*—Entire.

*Leaflet venation.*—Tri-nerved, not conspiciuos, 136C on upper and lower surface.

*Leaflet surface.*—Glabrous on upper surface and lower surface.

*Leaflet size.*—0.6 to 1 cm in width and 1.8 to 2.1 cm in length with upper most leaves 1 to 1.2 cm in length.

*Leaflet internode length.*—Average of 9 mm.

*Leaflet variegation pattern.*—Typically green with vertical mottling of pink with variable margins that may be white or pink, color intensity is dependent on sun exposure (less intense in shade).

*Leaflet color.*—Basal and cauline leaves: upper surface; a color between 133C and 198B with margin and mottling of 186C in full sunlight and 137D with margin NN155A to 4D with a tinged with 75C when leaves are shaded, lower surface; 191B with margins 186D in full sun and 138B with margin 4D when leaves are shaded.

*Rachis.*—Up to 20 cm in length including petiole with an average of 3 mm in width, upper surface is concave, glabrous surface, 146D in color.

*Petiole.*—Average of 7 cm in length and 3 mm in width, 146D in color, leaflets sessile.

*Foliage fragrance.*—None.

Flower description:

*Inflorescence type.*—Terminal and axillary cymes of single bell-shaped flowers.

*Lastingness of inflorescence.*—About 4 weeks from first opening bloom to fading of last opening bloom, individual blooms last about one week, flowers are self-cleaning.

*Flower shape.*—Bell-shaped.

*Flower number.*—5 to 8 per cyme.

*Flower fragrance.*—None.

*Flower buds.*—Ellipsoid in shape, average of 9 mm in length and 5 mm in diameter, 147A in color.

*Flower size.*—About 1.1 cm in length and about 2.3 cm in diameter.

*Flower aspect.*—Upward to outward.

*Peduncles.*—Average of 2 mm in length and 1 mm in width, 147D in color, glabrous surface.

*Pedicels.*—None, peduncles attached to stem.

*Calyx.*—Campanulate, comprised of 5 partially fused sepals.

*Sepals.*—5, ovate in shape, 4 mm in length and 2 mm in width, 147C to 147D in color on both surfaces, pubescent surface with transluscent hairs on both surfaces, base fused on lower half, acute apex, entire margin.

*Corolla form.*—Campanulate, petals fused at base.

*Petals.*—5, broadly ovate in shape, margin entire, acute apex, fused base, 8 to 9 mm in length and 7 mm in width, N88C in color on both surfaces when grown in shade and 93B in color when grown in full sun, glabrous on both surfaces.

*Bracteoles.*—Ovate in shape, an average of 8 mm in length and 4 mm in width, 137D with margin 145D in color on both surfaces, surface glabrous on both surfaces.

Reproductive organs:

*Gynoecium.*—1 Pistil, style is cylindrical in shape, average of 9 mm in length, <1 mm in width and 86B in color, stigma is tri-fid with arms <1 mm in length, and 156B to 156D in color, ovary is superior, conical in shape, 2 mm in length and width and 144A in color.

*Androecium.*—5 stamens, adnate to base of corrolla alternate to lobes, filament is N88D in color, 7 to 8 mm in length, <1 mm in width, anthers are 1 mm in length and <1 mm in width, attachment is basifixed, and 16C in color, pollen is moderate in quantity and 13D in color.

*Fruit/seed.*—Fruit and seed has not been observed to date.

It is claimed:

1. A new and distinct variety of *Polemonium* plant designated 'DUNKAL' as described and illustrated herein.

* * * * *